(12) United States Patent
Lina et al.

(10) Patent No.: US 6,506,947 B1
(45) Date of Patent: Jan. 14, 2003

(54) FLUORINATED DIOL AND METHOD FOR THE PRODUCTION THEREOF

(75) Inventors: Marie-Jose Lina, Lyons (FR); Eric Lacroix, Le Bourg (FR); Sophie Vanpoulle, Gif sur Yvette (FR); Gerard Orcel, Maison Laffite (FR); Robert Overton, Lenoir, NC (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/937,726

(22) PCT Filed: Mar. 29, 2000

(86) PCT No.: PCT/FR00/00778
§ 371 (c)(1),
(2), (4) Date: Dec. 20, 2001

(87) PCT Pub. No.: WO00/59856
PCT Pub. Date: Oct. 12, 2000

(30) Foreign Application Priority Data

Apr. 1, 1999 (FR) .............................................. 99 04093

(51) Int. Cl.$^7$ .......................... C07C 31/34; C07C 33/42; C07C 31/18; C07C 41/00
(52) U.S. Cl. ....................... 568/842; 568/843; 568/844; 568/845; 568/847; 568/853; 568/674; 568/675; 568/677; 568/678

(58) Field of Search .................................. 568/842, 843, 568/844, 845, 847, 853, 674, 675, 677, 678

(56) References Cited

U.S. PATENT DOCUMENTS 4,946,992 A * 8/1990 Falk et al.
5,567,794 A * 10/1996 Barraud et al.

FOREIGN PATENT DOCUMENTS

| DE | 23 36 913 | 2/1974 |
|----|-----------|--------|
| EP | 0 565 425 | 10/1993 |
| FR | 2712291 | 5/1995 |

* cited by examiner

*Primary Examiner*—Johann Richter
*Assistant Examiner*—Sikar A. Witherspoon

(57) ABSTRACT

The subject-matter of the invention is a fluorinated diol and its process of preparation. The fluorinated diol corresponds to the formula (I):

$$C_nF_{2n+1}-A-CH_2OCH_2-C(CH_2OH)_2-R$$

in which n has a value from 2 to 20 and A means $-CH=CH-$ or $-CH_2CH_2-$ and R is an alkyl group comprising 1 to 4 carbon atoms.

11 Claims, No Drawings

FLUORINATED DIOL AND METHOD FOR THE PRODUCTION THEREOF

FIELD OF THE INVENTION

A subject-matter of the invention is a fluorinated diol, used in particular for the preparation of a polymer material of polyurethane type for the coating of optical fibre, and its process of preparation.

BACKGROUND OF THE INVENTION

It is known that optical fibres comprise a double polymer coating composed of a plasticized primary coating in contact with the glass fibre which is topped by a secondary coating. This double coating protects the fibre from mechanical or chemical attacks which can cause attenuation faults for optical transmissions.

Each coating must possess good adhesion to the support which is intended for it and its physical properties must be compatible with the drawing conditions, in particular the drawing rate, and the final use of the fibre. The primary coating must absorb the possible stresses and microbends on the glass. The secondary coating confers, on the fibre, its mechanical properties.

Currently, primary and secondary coatings are coatings of the polyurethane-acrylate type which are photocrosslinked under U.V. radiation.

Application EP-A-0 565 425 discloses a polymer material of fluorinated polyurethane-acrylate type for the coating of optical fibre, which material is based on at least one diol, one diisocyanate and one acrylate, characterized in that at least one of the preceding compounds comprises fluorine and in that at least one of the preceding compounds comprises sulphur.

This material exhibits good mechanical characteristics, in particular an improved static fatigue resistance. However, it uses, for example, a sulphur-comprising diol, which implies high production costs because of the intermediate stage of preparation of the thiol, which results in by-products which have to be removed. The problem is the same with the other sulphur-comprising compounds used for the preparation of the material which is a subject-matter of Application EP-A-0 565 425.

There is thus a search for a material exhibiting the same mechanical properties but which does not involve sulphur-comprising products, in particular which does not involve sulphur-comprising diols.

There is thus a search in particular for a fluorinated diol which does not comprise sulphur.

DESCRIPTION OF THE INVENTION

Thus, the invention provides a fluorinated diol corresponding to the formula (I):

$$C_nF_{2n+1}-A-CH_2OCH_2-C(CH_2OH)_2-R$$

in which n has a value from 2 to 20 and A means —CH=CH— or —CH$_2$CH$_2$— and R is an alkyl group comprising 1 to 4 carbon atoms.

According to one embodiment, the fluorinated diol is unsaturated and corresponds to the formula:

$$C_nF_{2n+1}-CH=CH-CH_2OCH_2-C(CH_2OH)_2-R.$$

According to another embodiment, the fluorinated diol is saturated and corresponds to the formula:

$$C_nF_{2n+1}-CH_2CH_2-CH_2OCH_2-C(CH_2OH)_2-R.$$

According to one embodiment, in the formula (I), R is C$_2$H$_5$.

According to one embodiment, in the formula (I), n is an integer and is between 6 and 14 inclusive.

According to one embodiment, in the formula (I), C$_n$F$_{2n+1}$ results from a mixture and n is between 6 and 14 inclusive.

According to one embodiment, in the formula (I), n is between 6 and 8 inclusive.

The invention also provides a process for the preparation of a fluorinated diol according to the invention, when the latter is unsaturated, comprising the radical reaction of C$_n$F$_{2n+1}$I with the trimethylolalkane monoallyl ether, the alkane corresponding to the R group augmented by one carbon atom, and then the dehydroiodination.

The invention also provides a process for the preparation of a fluorinated diol according to the invention, when the latter is saturated, comprising the radical reaction of C$_n$F$_{2n+1}$I with the trimethylolalkane monoallyl ether, the alkane corresponding to the R group augmented by one carbon atom, and then the direct reduction.

The invention also provides a process for the preparation of a fluorinated diol according to the invention, when the latter is saturated, comprising the radical reaction of C$_n$F$_{2n+1}$I with the trimethylolalkane monoallyl ether, the alkane corresponding to the R group augmented by one carbon atom, and then the hydrogenolysis.

The invention also provides a process for the preparation of a fluorinated diol according to the invention, when the latter is saturated, comprising the radical reaction of C$_n$F$_{2n+1}$I with the trimethylolalkane monoallyl ether, the alkane corresponding to the R group augmented by one carbon atom, then the dehydroiodination and then the hydrogenation.

The fluorinated diol according to the invention is in particular devoid of sulphur.

The diisocyanates and the compounds comprising ethylenic unsaturation, such as vinyl ethers and acrylates, are the compounds conventionally used in the field under consideration. These compounds may or may not be fluorinated. The diisocyanate might be replaced by a polyisocyanate but, for the purposes of convenience, it is the first term which is used generically. Examples of such diisocyanate, acrylate and vinyl ether compounds can be found, for example, among the compounds mentioned in Application EP-A-0 565 425 and Application FR-A-2 712 291.

For the preparation of the coatings of fibres, the material according to the invention, which exhibits, inter alia, the distinguishing feature of being crosslinkable, is photocrosslinked, generally by U.V. radiation, preferably in the presence of a reactive diluent, generally a diacrylate, present in a conventional amount.

Use is conventionally made of photoinitiators and/or catalysts for (photo)chemical reactions, if required.

The fluorinated diols used in the invention are novel.

The fluorinated diols of the invention in which R is C$_2$H$_5$ are prepared by radical reaction of C$_n$F$_{2n+1}$I with allyloxytrimethylolpropane (or trimethylolpropane monoallyl ether), followed either by a dehydroiodination, optionally followed by a hydrogenation, or by a direct reduction or by a hydrogenolysis.

As the description is given with reference to the diol in which R is C$_2$H$_5$, it is clear that the other compounds are prepared in the same way starting from the appropriate monoallyl ether. This monoallyl ether is the trimethylolalkane monoallyl ether, the alkane corresponding to the R group augmented by one carbon atom.

The radical addition can be carried out according to well known procedures, either in bulk or in an organic solvent or in water.

Such a radical addition is disclosed in Patent Application DE-A-2 336 913, the reaction conditions of which may be followed.

Use may be made, as organic solvent, of acetone, tetrahydrofuran, dioxane, dimethylformamide, N-methyl-2-pyrrolidone, dimethyl sulphoxide, methyl ethyl ketone, methyl isobutyl ketone, ethanol, isopropanol and isopropyl acetate. Use will preferably be made of a water-soluble solvent or a mixture of water-soluble solvents.

The radical addition is generally carried out in the presence of (an) initiator(s) which is/are used in the proportion of 0.1 to 1.5% with respect to the total weight of the monomers charged, preferably 0.1 to 0.5%. Use may be made, as initiators, of peroxides, such as, for example, benzoyl peroxide, lauroyl peroxide, succinyl peroxide and tert-butyl perpivalate, or azo compounds, such as 2,2'-azobisisobutyronitrile, 4,4'-azobis(4-cyanopentanoic acid) and 2,2'-azobis(2-methylbutanenitrile).

The reaction temperature can vary within wide limits, that is to say between ambient temperature and the boiling point of the reaction mixture. The reaction is preferably carried out between 60 and 90° C. (the formation of polymers is thus avoided). With the same aim, it is possible to carry out the reaction by running in allyloxytrimethylolpropane, which makes it possible to control the reaction and to limit the rise in temperature.

An iodinated addition product is thus obtained.

The dehydroiodination is carried out using a strong inorganic base, such as sodium hydroxide or potassium hydroxide, or a strong organic base, such as DBU (1,8-diazabicyclo[5.4.0]undec-7-ene). The reaction is preferably carried out in an aqueous medium. The amount of strong base used is, for example, in the region of stoichiometry. The temperature is generally restricted to approximately 70–75° C. (the formation of polymers is thus avoided).

An unsaturated diol is thus obtained.

The saturated diols can be produced according to various methods. They can be obtained from the iodinated addition product by hydrogenolysis in the presence of an alkaline agent or else by reduction with sodium borohydride or zinc borohydride or lithium aluminium hydride or tributyltin hydride. They can also be obtained from the unsaturated derivative by catalytic hydrogenation according to known methods, without solvent or else in solution in a conventional organic solvent, such as ethanol or methanol, in the presence of a hydrogenation catalyst which can, depending upon the situation, be either Raney nickel or palladium-on-charcoal.

A saturated diol is thus obtained.

The perfluoroalkyl group $C_nF_{2n+1}$ can be linear or branched. The compound $C_nF_{2n+1}I$ is known per se and is prepared by conventional processes.

EXAMPLES

The following examples illustrate the invention without limiting it.

Example 1 a) $C_nF_{2n+1}$—$CH_2CHI$—$CH_2OCH_2$—$C(CH_2OH)_2$—$C_2H_5$: 125 grams by weight of a mixture of perfluoroalkyl iodides of formula: $C_nF_{2n+1}I$, where n is equal to 6,8,10,12 and 14 in respective ratios by weight of 63:25:8:2:2 (0.25 mol), in solution in 200 grams of acetone, and 64.5 grams of trimethylolpropane monoallyl ether (0.375 mol) are introduced into a one-liter reactor which is heated by a thermostatically-controlled jacket and is equipped with an anchor stirrer and a reflux condenser.

After rendering inert with nitrogen and heating to 62° C., the radical addition is initiated with 0.4 gram of azobisisobutyronitrile (AIBN) and then a further 0.2 gram of AIBN is added every 2 hours. The conversion of the perfluoroalkyl iodide $C_nF_{2n+1}I$ is monitored by gas chromatography. The reaction is complete after 20 hours. After evaporating the acetone under reduced pressure, the reaction mass is washed three times with 200 grams of demineralized water at 60° C. to remove the excess trimethylolpropane monoallyl ether. The addition product, in the form of a light yellow viscous liquid, is separated by settling and then dried under vacuum. It slowly crystallizes at ambient temperaure and its melting point is approximately 41° C. The yield with respect to the $C_nF_{2n+1}I$ is virtually quantitative.

b) $C_nF_{2n+1}$—$CH$=$CH$—$CH_2OCH_2$—$C(CH_2OH)_2$—$C_2H_5$: The same reaction is carried out on identical amounts in the same reactor as above. After separating by settling, the aqueous washing phase is removed by suction and then the addition product obtained is dehydroiodinated without being isolated. For this, it is maintained at 50° C. and an aqueous sodium hydoxide solution, i.e. 10.7 grams of sodium hydroxide (0.27 mol) in 50 grams of water, is run in dropwise over one hour, so as not to exceed 65° C. The conversion of the iodinated derivative is monitored by gas chromatography; it is complete after 7 hours. After separating by settling, the aqueous phase is removed by suction and then the organic phase is washed with demineralized water at 50° C. to neutrality. After separating the aqueous phase, the fluorinated diol obtained is dried by azeotropic distillation with cyclohexane. The solvent is subsequently distilled off under reduced pressure. A light yellow viscous liquid is then obtained with a yield of 95% with respect to the starting $C_nF_{2n+1}I$.

Example 2

The reaction is carried out as in Example 1, the $C_nF_{2n+1}I$ mixture being replaced by $C_6F_{13}$—I. The experimental conditions are the same and the iodinated addition derivative is obtained quantitatively in the form of a pale yellow solid which melts at 46° C.

The structure was confirmed by proton NMR (300 MHz, $CDCl_3$). The $\delta$ values are as follows:

4.42 ppm (—C$\underline{H}$—I, quintet, 1H), 3.60–3.80 ppm (—C$\underline{H}_2$—OH, complex unresolved peak, 4H), 3.54 ppm (—OC$\underline{H}_2$—C, singlet, 2H), 2.60–3.05 ppm (—C$\underline{H}_2CF_2$—, complex unresolved peak, 2H), 1.35 ppm (C$\underline{H}_2CH_3$, quartet, 2H), 0.86 ppm (CH$_2$C$\underline{H}_3$, triplet, 3H).

After dehydroiodination under the same conditions as in Example 1-b), a light yellow viscous liquid (ν≅1 300 cPs) with a relative density of 1.43 is obtained. It is a mixture comprising 1.3 mol % of starting diol, 73 mol % of the trans isomer of the unsaturated fluorinated diol and 25 mol % of the cis isomer of the unsaturated fluorinated diol. Proton NMR analysis (400 MHz, $CDCl_3$) gives the following signals:

Trans isomer:

6.45 ppm ($CF_2$—C$\underline{H}_A$=$CH_B$,DxTxt, $^3J_{HA-F}$=4.2 Hz, $^3J_{HA-HB}$=15.8 Hz, 1H), 5.90 ppm (CH$_A$=C$\underline{H}$B—CH$_2$—O, DxTxt, $^4J_{HB-F}$=12 Hz, 1H),
4.15 ppm (=CH—C$\underline{H}_2$O, complex unresolved peak, 2H),
3.55–3.75 ppm (C$\underline{H}_2$OH, complex unresolved peak, 4H),
3.50 ppm (O—C$\underline{H}_2$—C, singlet, 2H),
1.34 ppm (—C$\underline{H}_2$—CH$_3$, quartet, 2H),
0.85 ppm (—CH$_2$—C$\underline{H}_3$, triplet, 3H).

Cis isomer:
6.25 ppm (CF$_2$—C$\underline{H}_A$=CH$_B$, DxTxt, $^3J_{HA-F}$=2.5 Hz, $^3J_{HA-HB}$=12.5 Hz, 1H),
5.60 ppm (CH$_A$=C$\underline{H}_B$—CH$_2$—O, DxTxt, $^4J_{HB-F}$=15.5 Hz, 1H),
4.28 ppm (=CH—C$\underline{H}_2$O, complex unresolved peak, 2H),
3.55–3.75 ppm (C$\underline{H}_2$OH, complex unresolved peak, 4H),
3.44 ppm (O—C$\underline{H}_2$—C, singlet, 2H),
1.34 ppm (—C$\underline{H}_2$—CH$_3$, quartet, 2H),
0.85 ppm (—CH$_2$—C$\underline{H}_3$, triplet, 3H).

Example 3 a) 273 grams of perfluoroalkyl iodide C$_8$F$_{17}$—I (0.5 mol), washed beforehand at ambient temperature with an aqueous bisulphite solution to remove the traces of iodinated impurities, 93 grams of trimethylolpropane monoallyl ether (0.53 mol) and 120 grams of demineralized water are introduced into a 1-liter reactor which is heated by a thermostatically-controlled jacket and is equipped with an anchor stirrer and a reflux condenser. The heterogeneous mixture is rendered inert with nitrogen and then heated, with good stirring, to 70° C. 0.4 gram of AIBN initiator is then added. The reaction is exothermic and the jacket is cooled for several minutes in order not to exceed 90° C. The temperature is then maintained at 75° C. and the conversion of the reactants is monitored by gas chromatography. A further 0.2 gram of AIBN is added every two hours. The conversion of the C$_8$F$_{17}$—I is complete after 6 hours. The excess starting diol is removed by washing the organic phase three times with water at 75° C. Analysis of the latter confirms the presence of the expected addition product as the predominant compound. This intermediate rapidly solidifies (72° C.).

b) In the same reactor, the dehydroiodination reaction is linked in directly on the organic phase. 60 grams of water at 60° C. are added to the latter, maintained at 70° C., and then a solution comprising 20.3 grams of sodium hydroxide (0.5 mol) in 80 grams of water is run in dropwise over one hour, so as not to exceed 68° C. After 6 hours, analysis by GC shows that the reaction is complete. After separating by settling, the aqueous phase is removed by suction and then the organic phase is washed with demineralized water at 50° C. to neutrality. After separating the aqueous phase, the fluorinated diol obtained is dried by azeotropic distillation with cyclohexane. The solvent is subsequently distilled off under reduced pressure. A light yellow viscous liquid is then obtained with a yield of 95% with respect to the starting C$_8$F$_{17}$—I, which liquid slowly solidifies at ambient temperature (M.p.=38° C.). It is a mixture comprising 0.7 mol % of starting diol, 73.1 mol % of the trans isomer and 24.5 mol % of the cis isomer. Analysis by carbon-13 NMR (75.5 MHz, CDCl$_3$) gives:

for the trans isomer, the following signals:
138.8 ppm (CF$_2$—CH=$\underline{C}$H—, $^3J_{C-F}$=9 Hz),
117.3 ppm (CF$_2$—$\underline{C}$H=CH, $^2J_{C-F}$=23.7 Hz),
73.4 ppm (CH$_2$O—$\underline{C}$H$_2$—C—),
69.6 ppm (=CH—$\underline{C}$H$_2$O),
66.1 ppm (—$\underline{C}$H$_2$OH),
43 ppm ($\underline{C}$(CH$_2$OH)$_2$),
23.0 ppm (CH$_3$—$\underline{C}$H$_2$—),
7.4 ppm ($\underline{C}$H$_3$—CH$_2$—), for the cis isomer, the following signals:
142.3 ppm (CF$_2$—CH=$\underline{C}$H—, $^3J_{C-F}$=5.6 Hz),
117 ppm (CF$_2$—$\underline{C}$H=CH, $^2J_{C-F}$=23.7 Hz),
73.8 ppm (CH$_2$O—$\underline{C}$H$_2$—C—),
67.5 ppm (=CH—$\underline{C}$H$_2$O),
66.0 ppm (—$\underline{C}$H$_2$OH),
42.9 ppm ($\underline{C}$(CH$_2$OH)$_2$),
23.0 ppm (CH$_3$—$\underline{C}$H$_2$—),
7.4 ppm ($\underline{C}$H$_3$—CH$_2$—).

Example 4

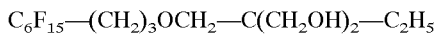

492 grams (1 mol) of C$_6$F$_{13}$— fluorinated diol described in Example 2, in 370 grams of methanol, 20 grams of 5% palladium-on-charcoal and 10 grams of K$_2$CO$_3$ are introduced into a stirred autoclave with a capacity of approximately 1 liter. Hydrogen is charged up to a pressure of 20 bar. The reaction is exothermic; the temperature rises to 50° C. while the pressure falls to 5 bar over 10 min. The autoclave is recharged with hydrogen to a pressure of 20 bar until hydrogen is no longer being absorbed. The reaction is then completed at 40° C. under 60 bar. Analysis by gas chromatography shows that all the unsaturated diol has been converted. The catalyst is separated by filtration and then the solvent is removed under reduced pressure. The structure of the saturated diol, obtained with a yield of 97%, is confirmed by proton NMR (400 MHz, CDCl$_3$):

The following are observed:
the disappearance of the signals at 6.45 and 6.25 ppm (CF$_2$—C$\underline{H}_A$=CH$_B$) of the cis/trans isomers,
the disappearance of the signals at 5.90 and 5.60 ppm (CH$_A$=C$\underline{H}_B$—CH$_2$—O) of the cis/trans isomers,
3.5 ppm (—CH$_2$—C$\underline{H}_2$O, triplet),
3.6–3.7 ppm (C$\underline{H}_2$OH, complex unresolved peak, 4H),
3.44 ppm (O—C$\underline{H}_2$—C, singlet, 2H),
2.15 ppm (CF$_2$—C$\underline{H}_2$—, broad multiplet),
1.89 ppm (CF$_2$—C$\underline{H}_2$—CH$_2$—, broad multiplet),
1.34 ppm (—C$\underline{H}_2$—CH$_3$, quartet, 2H),
0.85 ppm (—CH$_2$—C$\underline{H}_3$, triplet, 3H).

Example 5

62 grams (0.1 mol) of the C$_6$F$_{13}$— iodinated addition product described in Example 2, 13.8 grams (0.11 mol) of potassium carbonate as a fine powder, 160 grams of absolute ethanol and 6 grams of 5% palladium-on-charcoal catalyst are introduced into a stirred autoclave with a capacity of approximately 0.5 liter. After having purged with nitrogen, hydrogen is charged up to a pressure of 50 bar and heating is carried out at 60° C. with stirring. The pressure stabilizes at approximately 40 bar after 20 hours. The catalyst and the carbonate are separated by filtration and then the solvent is removed under reduced pressure. The viscous liquid obtained is redissolved in 200 ml of methylene chloride. The organic phase is washed with water to remove the KI and dried over sodium sulphate. After filtering and then removing the solvent, the viscous liquid obtained, which quickly solidifies, no longer comprises iodinated addition product (analysis by gas chromatography). 47 g (i.e. a yield of 95%) of the same product as in Example 4 are obtained.

Example 6

The reaction is carried out as in Example 4, the $C_6F_{13}$—diol being replaced by the $C_8F_{17}$—diol obtained in Example 3. Under identical conditions, the solid saturated fluorinated diol is obtained with a yield of 96%.

Example 7

610 g of 2,2,4-trimethylhexamethylene diisocyanate and 26.5 g of dibutyltin dilaurate are introduced into a 5-liter reactor. 715 g of the fluorinated diol of Example 2 are added and the mixture is left to react at 80° C. for 1 hour. The temperature is allowed to fall back to 40° C. and then 2.9 g of ionol, 492.7 g of hexamethylene diacrylate and 343.8 g of 22 hydroxyethyl acrylate are added. The reaction is allowed to continue until the disappearance of the isocyanate band at 2260 cm$^{-1}$ is observed by infrared analysis. 5% by weight of Irgacure 184 photoinitiator is then added.

A fibre is subsequently coated, the primary layer of which is a standard layer and the secondary layer of which is a layer made of the material obtained above. The photopolymerization is carried out under U.V. radiation.

Static fatigue is subsequently measured by the method with two bending points, lengths of fibres of 2.5 cm being coiled in high-precision glass tubes; 20 fibres are positioned per tube. 5 tubes with different diameters are used, imposing the following stresses on the fibres:

1. 456 kpsi (3 144 MPa)
2. 419 kpsi (2 889 MPa)
3. 399 kpsi (2 751 MPa)
4. 386 kpsi (2 661 MPa)
5. 353 kpsi (2 434 MPa)

The fibres under stress are placed in a controlled-environment chamber at 85° C. and 85% relative humidity. An acoustic detector triggers the automatic reading of the failure times for each of the fibres. The failure times as a function of the stresses applied are plotted as a logarithmic scale and the static fatigue factor n is calculated from the slope of the straight line obtained. In the case of the standard coating, a value of n of 18–20 is obtained, whereas, with the composition based on the fluorinated diol according to the invention, the value of n is 23.

The invention is not limited to the embodiments described; the fluorinated diol can have other applications, such as use as a surface-modifying agent, in particular as an oleophobic and/or hydrophobic agent.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

What is claimed is:

1. A fluorinated diol corresponding to the formula (I):

$$C_nF_{2n+1}-A-CH_2OCH_2-C(CH_2OH)_2-R$$

in which n has a value from 2 to 20 and A means —CH=CH— or —CH$_2$CH$_2$— and R is an alkyl group of 1 to 4 carbon atoms.

2. A fluorinated diol according to claim 1, which is unsaturated and corresponds to the formula:

$$C_nF_{2n+1}-CH=CH-CH_2OCH_2-C(CH_2OH)_2-R.$$

3. A fluorinated diol according to claim 1, which is saturated and corresponds to the formula:

$$C_nF_{2n+1}-CH_2CH_2-CH_2OCH_2-C(CH_2OH)_2-R.$$

4. A fluorinated diol according to claim 1, 2 or 3, in which R is $C_2H_5$.

5. A fluorinated diol according to any one of claims 1 to 4, in which, in the formula (I), n is an integer and is between 6 and 14 inclusive.

6. A fluorinated diol according to any one of claims 1 to 4, in which, in the formula (I), $C_nF_{2n+1}$ results from a mixture and n is between 6 and 14 inclusive.

7. A fluorinated diol according to any one of claim 1 to 6, in which, in the formula (I), n is between 6 and 8 inclusive.

8. A process for the preparation of a fluorinated diol according to any one of claims 1, 2, 4, 5, 6 or 7, comprising the reaction of $C_nF_{2n+}I$ with trimethylolalkane monoallyl ether, the alkane corresponding to R group augmented by one carbon atom, and then the dehydroiodination.

9. A process for the preparation of a fluorinated diol according to any one of claims 1, 3, 4, 5, 6 or 7, comprising the reaction of $C_nF_{2n+}I$ with trimethylolalkane monoallyl ether, the alkane corresponding to the R group augmented by one carbon atom, and then the direct reduction.

10. A process for the preparation of a fluorinated diol according to any one of claims 1, 3, 4, 5, 6 or 7, comprising the reaction of $C_nF_{2n+1}$ with trimethylolalkane monoallyl ether, the alkane corresponding to R group augmented by one carbon atom, and then the hydrogenolysis.

11. A process for the preparation of a fluorinated diol according to any one of claims 1, 3, 4, 5, 6 or 7, comprising the reaction of $C_nF_{2n+1}I$ with the trimethylolalkane monoallyl ether, the alkane corresponding to R group augmented by one carbon atom, then the dehydroiodination and then hydrogenation.

* * * * *